(12) United States Patent
Schuh et al.

(10) Patent No.: US 10,010,435 B2
(45) Date of Patent: Jul. 3, 2018

(54) ORTHOPEDIC DAMPING DEVICE (71) Applicant: OTTO BOCK HEALTHCARE GMBH, Duderstadt (DE)

(72) Inventors: Andreas Schuh, Duderstadt (DE); Clemens Kimmig, Oppenau (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 15/025,990

(22) PCT Filed: Oct. 10, 2014

(86) PCT No.: PCT/EP2014/002744
§ 371 (c)(1),
(2) Date: Mar. 30, 2016

(87) PCT Pub. No.: WO2015/051918
PCT Pub. Date: Apr. 16, 2015

(65) Prior Publication Data
US 2016/0213495 A1    Jul. 28, 2016

(30) Foreign Application Priority Data
Oct. 10, 2013   (DE) .................. 10 2013 016 800

(51) Int. Cl.
*F16F 9/02* (2006.01)
*A61F 2/68* (2006.01)
(Continued)

(52) U.S. Cl.
CPC .................. *A61F 2/68* (2013.01); *A61F 2/60* (2013.01); *A61F 2/64* (2013.01);
(Continued)

(58) Field of Classification Search
CPC ...... A61F 2/60; A61F 2/64; A61F 2/68; A61F 2002/74; A61F 2002/745; A61F 2002/747;
(Continued)

(56) References Cited

U.S. PATENT DOCUMENTS 2,859,451 A * 11/1958 Mauch ...................... A61F 2/64
623/39
5,199,537 A * 4/1993 Worner ................. F16F 9/0209
188/266
(Continued)

FOREIGN PATENT DOCUMENTS

DE         19709593 A1    12/1997
DE      202004008014 U1     9/2004
(Continued)

OTHER PUBLICATIONS

PCT International Search Report for PCT International Patent Application No. PCT/EP2014/002744, dated Feb. 11, 2015.

*Primary Examiner* — Thomas J Williams
(74) *Attorney, Agent, or Firm* — Holland & Hart (57) ABSTRACT

An orthopedic damping device with a movably mounted piston and at least one chamber which has a wall and in which a compressible medium is compressed by moving the piston in a first direction and decompressed by moving the piston in an opposite second direction. The chamber is connected to a discharge channel. A closure element is paired with the discharge channel. The closure element is movably mounted on a support. The support is coupled to the piston or is designed as a piston. The closure element is coupled to a contact region which can be moved relative to the support.

27 Claims, 9 Drawing Sheets

(51) Int. Cl.
  *A61F 2/60* (2006.01)
  *A61F 2/64* (2006.01)
  *F16F 9/34* (2006.01)
  *A61F 2/74* (2006.01)

(52) U.S. Cl.
  CPC ... *A61F 2002/745* (2013.01); *A61F 2002/747* (2013.01); *F16F 9/0281* (2013.01); *F16F 9/34* (2013.01)

(58) Field of Classification Search
  CPC ..... A61F 2002/748; F16F 9/02; F16F 9/0209; F16F 9/0227; F16F 9/0281; F16F 9/34; F16F 9/3405; F16F 9/342
  USPC .... 188/313, 318, 322.13; 267/117, 119, 124
  See application file for complete search history.

(56) References Cited

U.S. PATENT DOCUMENTS

| | | | | |
|---|---|---|---|---|
| 6,364,075 B1 * | 4/2002 | Lemmens | ............... | F16F 9/346 188/282.1 |
| 7,413,062 B2 * | 8/2008 | Vandewal | .......... | B60G 17/0152 188/266.5 |
| 8,689,954 B2 * | 4/2014 | Kamioka | ............... | F16F 9/0209 188/322.13 |
| 2005/0040574 A1 * | 2/2005 | Ivers | .................... | F16F 9/0218 267/113 |
| 2005/0156366 A1 | 7/2005 | Muller | | |
| 2007/0208431 A1 | 9/2007 | Bisinger et al. | | |
| 2013/0123941 A1 | 5/2013 | Boiten | | |

FOREIGN PATENT DOCUMENTS

| | | |
|---|---|---|
| DE | 202009012627 U1 | 12/2009 |
| DE | 202009016261 U1 | 3/2010 |
| DE | 102010031723 A1 | 1/2012 |
| EP | 1537803 A1 | 6/2005 |
| GB | 737486 | 9/1955 |
| GB | 982527 | 2/1965 |
| WO | 96/25898 A1 | 8/1996 |
| WO | 00/74610 A1 | 12/2000 |
| WO | 00/76429 A1 | 12/2000 |

* cited by examiner

ORTHOPEDIC DAMPING DEVICE

TECHNICAL FIELD

The invention relates to an orthopedic damping device with a movably mounted piston and at least one chamber which has a wall and in which a compressible medium is compressed by moving the piston in a first direction and decompressed by moving the piston in an opposite, second direction.

BACKGROUND

The orthopedic damping device can be used in particular in orthotic joints or prosthetic knee joints, but can also be used in principle in order to improve the behavior of pneumatic dampers.

With use of orthopedic damping devices that use a compressible medium, the medium is compressed in a compression chamber by reducing the chamber volume by means of a piston. The piston can be formed both as a linearly displaceable piston and as a rotary piston. If the force exerted onto the piston is reduced, for example in the event of a movement reversal, the compressed medium, for example air, is decompressed and exerts a restoring force. In the case of prosthetic or orthotic joints, this may lead to a catapult effect of a joint component, for example in the case of a lower leg component, which is disadvantageous in particular at high movement speeds.

SUMMARY

The object of the present invention is to provide an orthopedic damping device with which an improved adaptability of the expansion behavior and in particular of the extension behavior can be achieved.

This object is achieved in accordance with the invention by an orthopedic damping device having the features of the main claim. Advantageous embodiments and developments of the invention are disclosed in the dependent claims, the description, and the drawings.

In the orthopedic damping device according to the invention with a movably mounted piston and at least one chamber which has a wall and in which a compressible medium is compressed by moving the piston in one direction and decompressed by moving the piston in an opposite, second direction, the chamber is connected to an outlet channel, the outlet channel is assigned a closure element, the closure element is movably mounted on a support, the support is coupled to the piston or is formed as a piston, and the closure element is coupled to a contact region which can be moved relative to the support. As a result of this embodiment it is possible to provide a position-independent and direction-controlled venting of the chamber and to release the outlet channel at the moment when there is no longer any compression of the medium and the medium should be decompressed. Due to the position-independent and direction-controlled venting at the moment of reversal, for example from a flexion to an extension, it is possible on the one hand to utilize the damping and cushioning effect by the compression of the medium in the chamber and on the other hand to prevent a restoring movement from being forced by the pressure on the piston or to prevent the restoring tendency from being reduced. In preferred embodiments the support serves as an actuation element for the closure element. If reference is made hereinafter to a damping device, this is an orthopedic damping device, in particular for orthotic joints or prosthetic joints, in particular for knee joints. The support can be formed as a piston, piston rod, cylinder wall, chamber wall in a blocking element, or as a blocking element.

In accordance with a development the contact region to which the closure element is coupled is the wall of the chamber or the wall of a blocking element, which wall is arranged in the chamber or in a region coupled in terms of force or movement.

The piston may be formed as a rotary piston or cylindrical piston having a linear, reciprocal movement path.

The outlet channel may lead into the surrounding atmosphere or into a second chamber. In the embodiment with two chambers it is possible for the outlet channel to lead into the oppositely acting chambers, these being the flexion chamber and the extension chamber in the case of a joint device.

A sound damper may be arranged in or on the outlet channel in order to reduce the noise of the escaping medium. This is advantageous in particular in the case of orthotics or prosthetics in order to minimize the ejection noise for the user of the damping device and the surrounding environment.

The closure element can be mounted frictionally and slidingly on the contact region, such that the switchover of the closure element from the closed state to the open state can be performed by a frictional force.

The outlet channel can be guided through the piston itself, whereby a solution of simple design is provided.

The closure element can be resiliently pre-loaded against the contact region, whereby it is possible for a uniform contact force to be present in the contact region. The closure element is therefore self-adjusting, wherein a tensioning element can be provided, via which the frictional force of the closure element can be adjusted.

The closure element can be formed as a piston ring and can be mounted in a piston ring groove, such that the compression of the compressible medium, in particular air, is ensured in one direction, and in the other movement direction, due to the provision of a sufficient play and an outlet channel, the compressed air can escape through the outlet channel in the event of a reverse movement of the piston.

The closure element may also be mounted on a piston rod and in a blocking element surrounding the piston rod. The blocking element may be arranged within the cylinder, in which the piston is guided. The blocking element may delimit the respective chambers and may be arranged fixedly in the housing or the cylinder. The blocking element may also take on the function of the support. In the closing state, the closure element may bear against a seal surrounding the outlet channel, wherein the seal may be formed as an O-ring, which is arranged around the outlet channel and protrudes slightly beyond said channel, such that an airtight closure of the outlet channel is provided by the abutment of the closure element against the seal.

A second chamber can be arranged on the side of the piston opposite the first chamber, in which second chamber the compressible medium is compressed. In the event of an embodiment of this type, a double-acting piston is provided, which can be used to damp both the extension and flexion movement or the movement in a first and in a second direction. Depending on the orientation of the outlet channel and the closure element, the restoring force can be adjusted in each case by the expanding medium. It is also possible for both chambers to be coupled to an outlet channel and a closure element for direction-controlled venting of the respective chamber.

The blocking element can be mounted in a stationary manner in a housing forming the chambers, and it is possible by way of example for the blocking element to separate the first chamber from a double-acting damping cylinder, such that at least three chambers are formed on the whole, of which two are arranged on the other side of the blocking element.

The closure element can be coupled to the piston via a switching element, such that there is no need for a direct assignment of the closure element to the piston or the contact region.

The closure element and/or the outlet channel can be adjustably mounted or formed so as to be able to adjust the degree of maximum venting. Due to the adjustable embodiment, the closure element may also be completely deactivated if there is no desire for rapid venting.

In accordance with a development of the invention the chamber tapers conically in the direction of an end position of the piston. As a result of the tapering, the distance between the closure element and the cylinder wall or the chamber is reduced in the region of the end position, such that there is improved contact between the closure element and the chamber wall when the contact region is part of the chamber wall. Here, a comparatively small conicity is sufficient to obtain an improvement of the response behavior of the closure element. The embodiment of a conically tapering chamber can be provided by rolling, whereby a smoothing and strain hardening of the surface of the chamber are achieved in addition. The conicity can be provided over the entire length of the chamber or also only over a certain part. The cone angle may be between 0.2° and 1°, preferably 0.5°. Alternatively to a conical tapering of a chamber or a cylinder bore in the end region of the piston movement, it is also possible and is provided, in an embodiment of the support as piston rod, for this piston rod to have a widening, i.e. diameter increase, in the region of the end position. If the closure element or the switching element bears against the piston rod externally, the pressure and thus the frictional force increase in the region of the widening, which leads to a secure switching arrangement. The widening may also change in a constant manner over the entire path of relative displacement between support and switching or closure element or only in portions, such that an enlargement is provided only in certain portions.

The support can be arranged in a stationary manner inside the chamber and may thus cause a chamber division. The piston rod may pass through the support or a chamber delimitation.

The second chamber, which is fluidically connected to the first chamber, is advantageously formed as an open chamber and has a lower internal pressure compared with the first chamber when the first chamber is compressed. A counter pressure going beyond the ambient pressure is not established in the second chamber. It is thus possible that an undesirable spring effect, for example at the end of a flexion movement, will occur across the damping device on account of the enclosed air volumes. Rather, in the event of a minor return movement, i.e. extension, the outlet opening of the outlet channel is opened by the closure element, such that the overpressure prevailing in the first chamber is relieved and a spring-back effect is avoided. Ambient pressure preferably prevails in the second chamber.

BRIEF DESCRIPTION OF THE DRAWINGS

Exemplary embodiments of the invention will be explained in greater detail hereinafter on the basis of the accompanying figures, in which.

DETAILED DESCRIPTION

Figure 1:
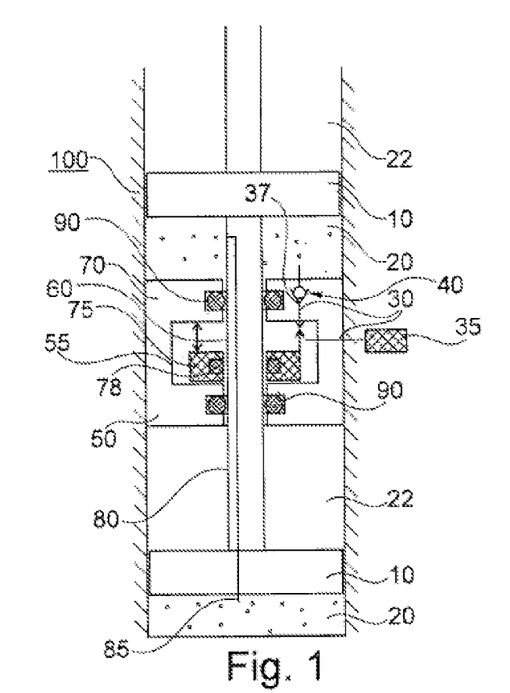
FIG. 1 shows a schematic sectional illustration of a damping device.

FIG. 1 shows a schematic sectional illustration of a damping device having a housing 100, in which two pistons 10 are arranged so as to be longitudinally movable. The pistons 10 are interconnected by a piston rod 80 and, together with the housing and a support 50, form two first chambers 20, in which the medium disposed therein, for example air, is compressed in the event of a downwardly directed movement. Between the lower piston 10 and the lower edge of the support 50, there is formed a second chamber 22, which is likewise filled with the compressible medium, wherein in the event of a movement in the opposite direction, i.e. in the event of a movement of the lower piston 10 in the direction of the support 50, the medium is compressed. The damping device can be used for example in prosthetics and orthotics, for example in prosthetic knee joints or orthotic knee joints, wherein, in accordance with the preferred situation of installation, on account of the high forces occurring, the two first chambers 20 counteract a flexion in the case of a knee joint, whereas the second chamber 22 counteracts an extension. Accordingly, the first chambers 20 can be referred to as flexion chambers and the second chamber 22 can be referred to as an extension chamber.

The piston rod 80 is guided through the support 50, and seals 90 bear against the piston rod 80, such that a substantial gastight termination is provided and no medium can flow from the upper flexion chamber 20 into the extension chamber 22 through the support 50. Seals (not illustrated) are arranged on the piston 10 that likewise prevent the compressed medium from flowing past along the outer wall. An unwanted passage of gas from the flexion chamber 20 into the extension chamber or into the surrounding environment is therefore impossible. Provided an upper-side termination is provided, a second extension chamber 22 can be formed above the upper piston 10.

The lower piston 10 and the piston rod 80 are provided with a connection channel 85, such that the lower flexion chamber 20 and the upper flexion chamber 20 are fluidically connected to one another. An actuator chamber 55 is formed inside the support 50 and can be embodied as an annular space, in which a switching element 75 is arranged. The switching element 75 is mounted frictionally on the piston rod 80 via a sliding and friction element 78, which can be formed as an O-ring, for example. The actuator chamber 55 is dimensioned such that the switching element 75 can be moved over a certain switching path. The switching path is indicated by the double-headed arrow.

A closure element 40 in the form of a switching valve is arranged inside the support 50 and is connected to the actuator chamber 55 via an outlet channel 30. When the closure element 40 is open, air can pass from the flexion chamber 20 into the actuator chamber 55 and from there can escape into the surrounding environment through a sound damper 35 via a further outlet channel 30. The damping device according to FIG. 1 compresses the compressible medium in the event of a downward movement of the piston 10 due to the reduction of the chamber volumes of the flexion chambers 20, wherein, on account of the connection channel 85, a pressure compensation is implemented between both flexion chambers 20. On account of the orientation of the closure element 40 in the form of a check valve, no air can escape from the upper flexion chamber 20 through the outlet channel 30. On account of the friction between the switching element 75 and the piston rod 80, for example on account of the O-ring seal 78, the switching element 75 is slid against the lower delimitation of the actuator chamber 55, wherein a possible coupling of the switching element 75 to the closure element 40 is disengaged. On account of the high compression within the flexion chambers 20, in the event of a movement reversal of the joint, i.e. in the event of an extension, the involved joint components tend to spring forward or tend to extend very quickly and provide movement support, which may lead to an unwanted course of movement. In the event of a movement reversal of the piston 10 and therefore also of the piston rod 80, the switching element 75 is also moved in the direction of the extension movement, which is indicated by the double-headed arrow. In the event of an upward movement of the switching element 75, the check valve or closure element 40 is opened via an actuation element, for example a pin, such that the compressible medium inside the flexion chambers 20 escapes from the outlet channels 30 into the surrounding environment through the sound damper 35. The closure element 40 is held open as long as the switching element 75 is in the switching position, for example at the upper end of the actuator chamber 55. In the event of a renewed movement reversal, i.e. an additional flexion, the switching element 75 is disengaged from the closure element 40, and the chamber volumes within the flexion chambers 20 are closed again, such that an effective flexion damping can be achieved on account of the pneumatic compression.

The switching element 75 is thus coupled to the closure element 40 via a contact region 60, which corresponds substantially to the length of the stroke of the piston rod 80.

The switching element 75, in the exemplary embodiment shown in FIG. 1, presses against a tappet 37, which in FIG. 1 projects into the actuator chamber 55 from above. The tappet 37 is movably mounted and, as the switching element 75 is raised, is displaced into the support 50 and in this way opens the closure element 40.

Figure 2:
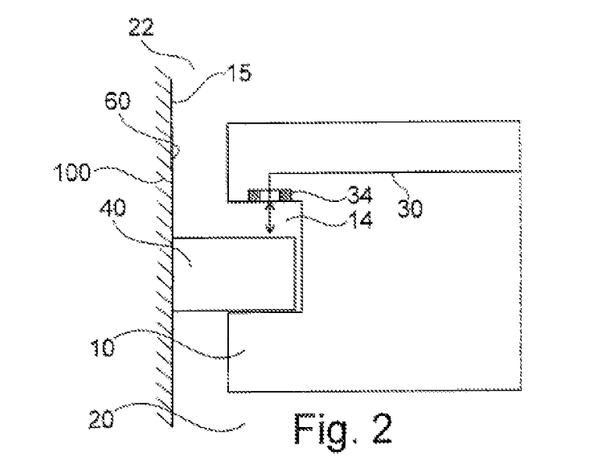
FIG. 2 shows a detailed view.

A variant of the invention is illustrated in FIG. 2, in which a detailed view of the damping device is shown. The piston 10 is mounted inside the housing 100 so as to be movable back and forth along a cylinder wall 15. A piston ring groove 14 is formed on the piston periphery, in which groove a piston ring is arranged as closure element 40. The piston ring groove 14 has an oversize relative to the width of the piston ring, such that the piston ring 40 as closure element has a slight play in the direction of movement of the piston 10. The possibility of relative movement is indicated by the double-headed arrow. A small amount of play is provided between the outer periphery of the piston 10 and the wall 15 of the cylinder and has been illustrated in an exaggerated manner in FIG. 2. The piston ring 40 widens radially outwardly and bears movably against the wall 15. The wall 15 at the same time forms the contact region between the closure element 40 and the piston 10, which is in turn formed as a support for the closure element 40. An outlet channel 30 is formed inside the piston 10 and is oriented substantially perpendicularly to the wall 14 of the cylinder. A seal 34, for example in the form of an O-ring, is arranged around the opening of the outlet channel 30 in the region of the groove wall oriented perpendicularly to the wall 15. In the event of an upward movement of the piston 10, the piston ring 40 will be pressed within the piston ring groove 14 in the direction of the side wall opposite the seal 34 on account of the friction, such that a gap between the chamber 20 and the outlet channel 30 is opened. A compressible medium can pass through between the wall 15, the piston outer diameter 10 and the gap between the piston ring 40 and the groove 14, into the outlet channel 30 and from there can escape into the surrounding environment, for example via a piston rod. In the event of a movement reversal, when a flexion movement is introduced, the piston 10 is moved downwardly, and on account of the friction of the piston ring 40 this component acting as closure element is pressed against the seal 34, such that the outlet channel 30 is closed. During the flexion movement, the flexion chamber 20 remains closed, such that the medium is compressed. On account of the construction, it is possible to achieve a load-independent, direction-controlled venting of the flexion chamber 20 or flexion chambers 20.

Figure 3:
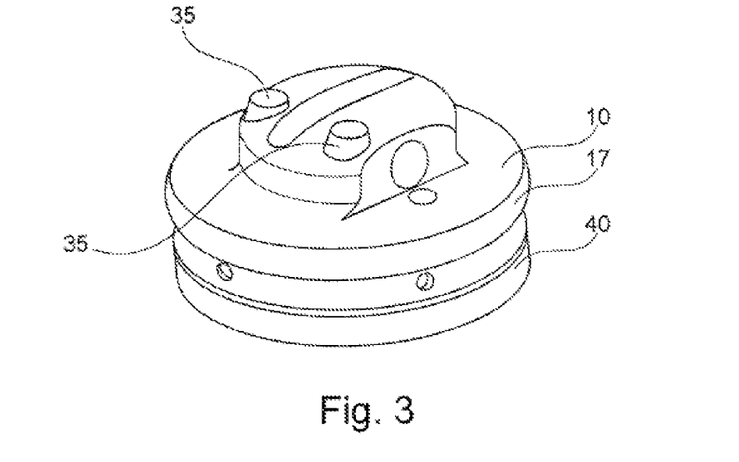
FIG. 3 shows a perspective illustration of a piston.

A piston 10 with the piston ring 40 at the outer periphery is illustrated in FIG. 3. The piston ring is inserted in the piston ring groove 14, and a further ring seal 17 is arranged above the piston ring in order to seal off the flexion chamber with respect to unwanted venting. Two sound dampers 35 for outlet channels are provided in the region of the piston rod receptacle.

Figure 4:
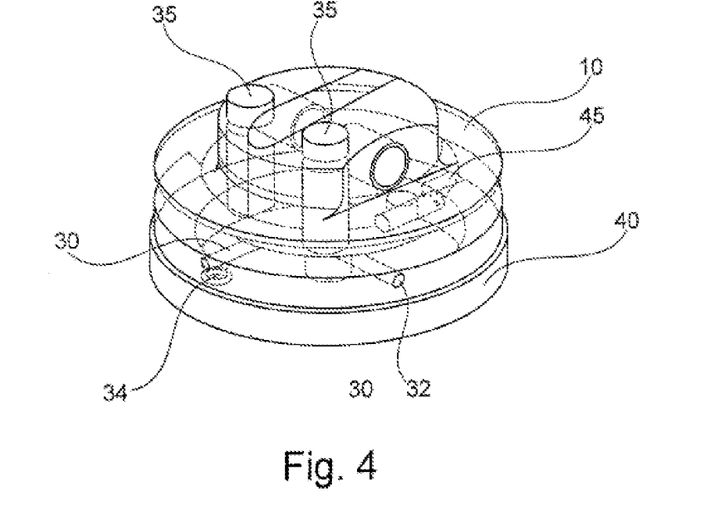
FIG. 4 shows a partially transparent illustration of a piston.

The piston 10 is shown in FIG. 4 in a partially transparent illustration. The upper ring seal 17 has been removed, and the piston ring 40 is inserted as closure element in the groove. It can be seen that the outlet channels 30 are formed within the piston 10 via transverse bores, which are guided radially inwardly. The outlet channels 30 are closed by stoppers 32. The seal 34 on the upper side wall of the piston ring groove can be seen inside the groove 14. The air from the flexion chamber passes via the outlet channels 30 through the sound dampers 35 into the surrounding atmosphere. A tensioning element 45 for the closure element 40 is arranged opposite the seal 34, with which tensioning element it is possible to achieve and maintain a radial pre-load, such that a constant pressing force is ensured over a long period of time.

Figure 5:
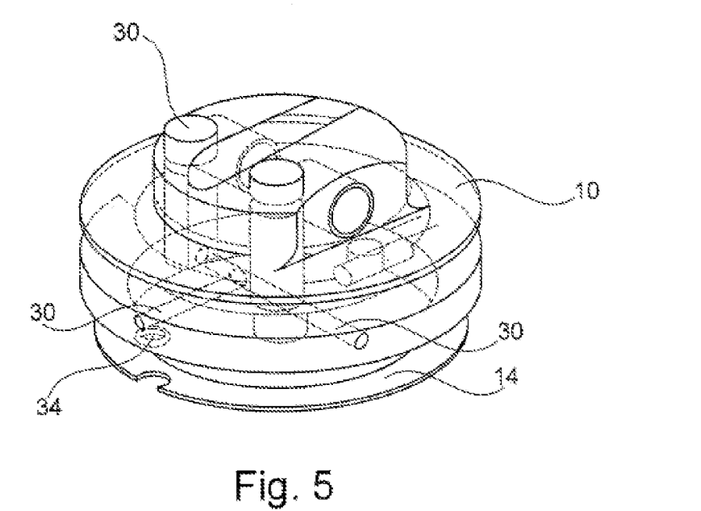
FIG. 5 shows an illustration of a piston with air channels marked out.

FIG. 5 shows the piston 10 in a partially transparent illustration without ring seal 17 and without closure element 40. The piston ring groove 14 can also be seen, as can the recess, arranged thereabove, for the ring seal 17. A bore can be seen inside the piston ring groove 14 in the lower side wall, which bore is provided for manufacturing reasons in order to achieve the right-angled channel guidance of the outlet channels 30 and the connection to an opening in one of the side walls of the piston ring groove 14. The outlet channels 30 are shown dark in the illustration.

Figure 6:
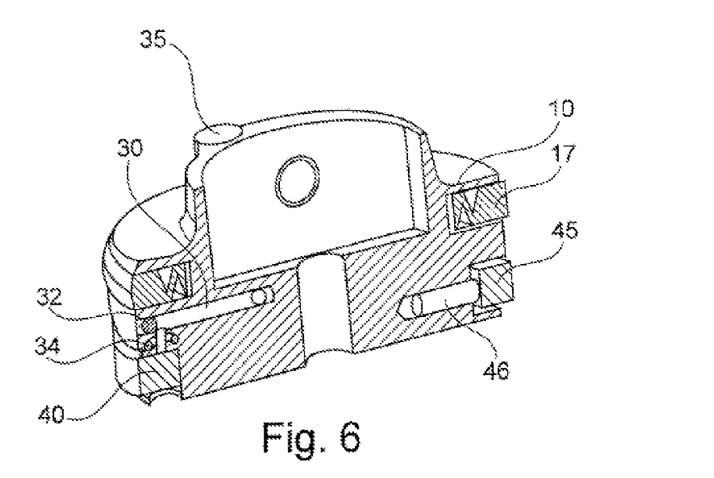
FIG. 6 shows a sectional illustration of the piston.

In FIG. 6 the piston 10 is shown in a sectional illustration, on the basis of which the closure element 40 and the seal 34 around the bore opening in a side wall of the piston ring groove 14 can be seen. The stopper 32 closes the outlet channel 30 radially outwardly, and the transverse bore formed within the outlet channel 30 leads to the sound damper 35 and discharges the compressed air into the surrounding environment in the event of a direction reversal of the piston 10. The tensioning element 45 in the region of the outer wall of the piston 10 for radial widening of the closure element 40 is likewise shown. The tensioning element 45 may be assigned an adjustment element 46, with which it is possible to adjust the tensioning element 45. Alternatively or additionally, the adjustment element 46 may also be used as a positioning aid, by means of which the tensioning element 45 is secured with respect to a rotation about the cylinder longitudinal axis. Here, the adjustment element 46 can be formed as a separate component, which is arranged in the indentation or the slot provided for this purpose and engages with a recess or indentation on the tensioning element 45 and thus prevents a rotation. Alternatively, the adjustment element 46 can also be fixedly connected to the tensioning element 45 and can engage with the indentation, bore or recess in order to prevent the rotation of the tensioning element 45.

Figure 7:
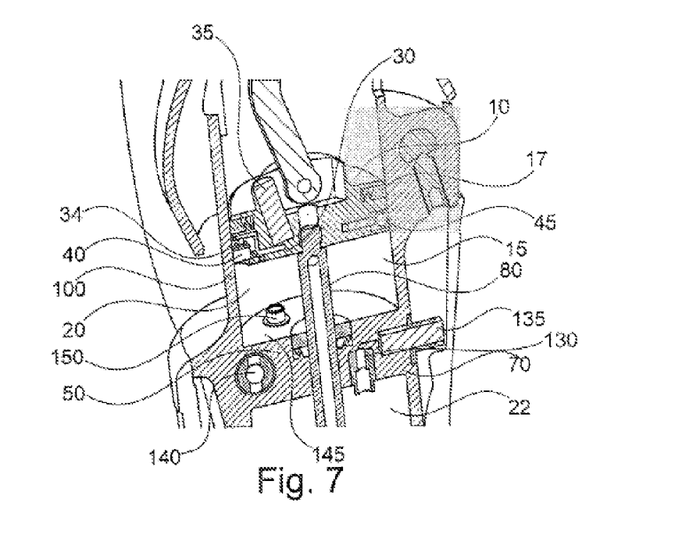
FIG. 7 shows a perspective sectional illustration of a first embodiment.

The piston according to FIGS. 3 to 6 is illustrated in FIG. 7 as an upper termination of a damping device having a housing 100. The piston 10 is moved by way of example via a thrust rod, which is connected to an upper joint component, along the longitudinal extension of the piston rod 80 in the cylinder of the housing 100. If the piston 10 is moved together with the piston rod 80 downwardly, i.e. in the direction of the support 50, the air inside the flexion chamber 20 will be compressed. On account of the friction of the closure element 40 at the outer wall of the cylinder, the closure element is moved in the direction of the seal 34, the outlet channels 30 are closed, and no air can escape from the sound damper 35 into the surrounding environment. The ring seal 17 offers an additional sealing of the flexion chamber 20. If a reverse movement is introduced, i.e. an extension, the piston 10 moves upwardly, the closure element 40 is pressed in the direction of the lower piston ring groove wall, and the channel 30 is opened. Air can flow from the flexion chamber 20 through the bores within the piston, past the seal 34, into the surrounding environment. The extension chamber likewise has an outlet channel 130 and a sound damper 135, via which air can be discharged from the extension chamber 22 into the surrounding environment during the extension movement, and it is also possible for air from the surrounding environment or from the extension chamber 22 to pass in a controlled manner into the flexion chamber 20 via an overflow valve 150, for example when the flexion chamber 20 has been completely vented in the case of an interruption of the extension movement and in addition an extension takes place in order to prevent a negative pressure from forming within the flexion chamber 20. A separate outlet channel 140 is for this purpose arranged between the flexion chamber 20 and extension chamber 22, in which separate outlet channel an additional sound damper 145 (not visible in FIG. 7) can be positioned. The overflow valve 150 is advantageously likewise formed as a check valve. Air is also guided from the flexion chamber 20 into the extension chamber 22 when the flexion chambers 20 are to be vented and where appropriate the extension chambers 22 are to be aerated.

Figure 8:
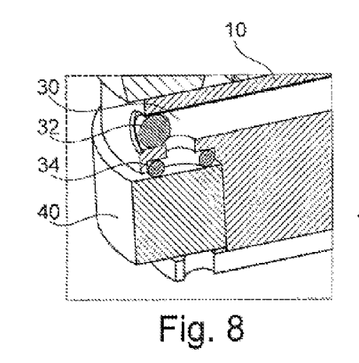
FIG. 8 shows a detailed illustration of a closure element in the closed position.

FIG. 8, in a detailed view, shows the position of the closure element 40 during the flexion movement. It can be clearly seen that the closure element 40 bears in the form of the piston ring against the seal 34 and terminates the outlet channel 30 in a sealing manner.

Figure 9:
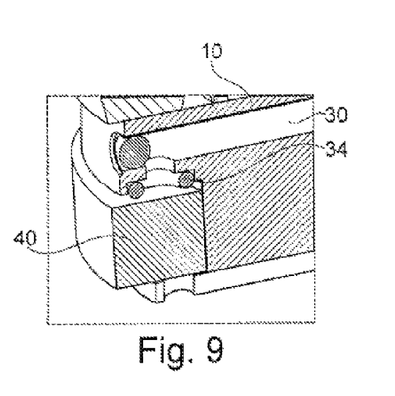
FIG. 9 shows a detailed illustration according to FIG. 8 in the open position.

FIG. 9 shows the position of the closure element 40 during an extension movement, it being possible to see a gap between the closure element 40 and the upper piston ring groove wall, whereby the permeability from the flexion chamber to the outlet channel 30 is ensured.

Figure 10:
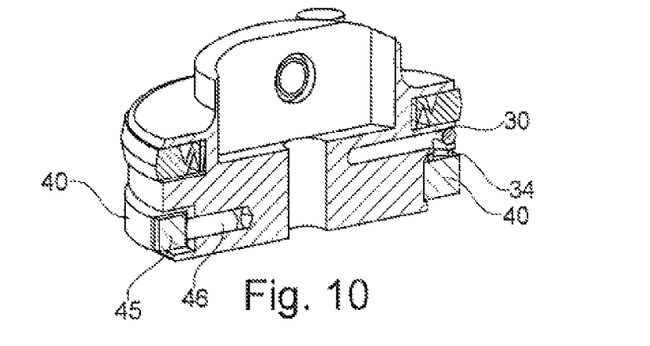
FIG. 10 shows an overall sectional illustration of a piston.

FIG. 10, in a sectional illustration, shows the tensioning element 45 with the adjustment element 46, which causes the piston ring 40 or the closure element to be pressed against the cylinder wall. The frictional force between the closure element 40 and the contact region, i.e. the cylinder wall of the damping device, can be controlled via the tensioning element 45 and the adjustment element 46. The greater the pre-load and radial widening of the closure element is, the greater the friction is and the more exactly and precisely the closure element responds to a direction reversal. In addition to the friction adjustment, a compensation of wear is also achieved via the tensioning element 45.

As already discussed, the adjustment element 46 can also be provided in a non-adjustable embodiment. In this case it serves merely as a positioning element, by means of which a rotation of the tensioning element 45 about the longitudinal axis of the piston 80 is prevented.

Figure 11:
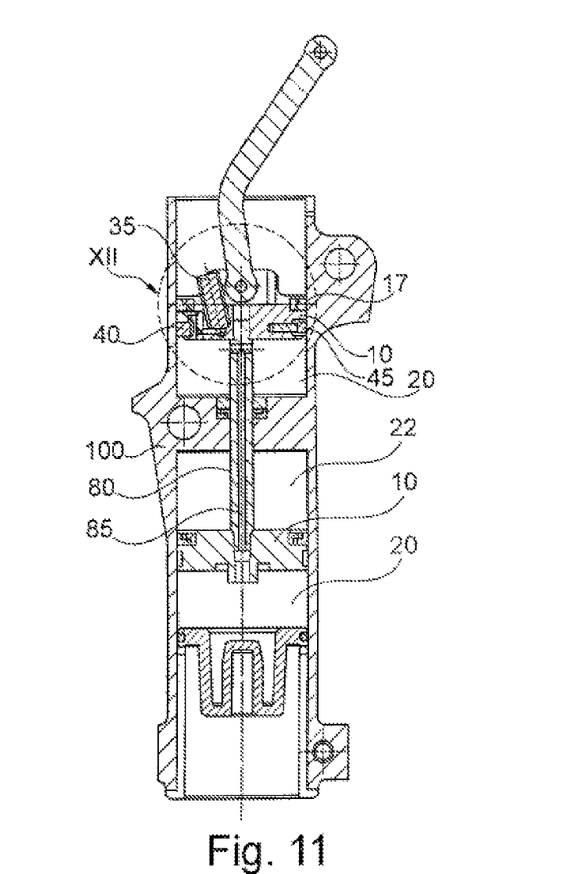
FIG. 11 shows a sectional illustration of a variant of the invention.

FIG. 11 shows a sectional illustration of the complete damping device, in which two flexion chambers 20 and an extension chamber 22 are arranged. The two flexion chambers 20 are fluidically coupled to one another via the piston rod 80 and the connection channel 85. The structure of the piston 10, which closes the upper flexion chamber 20, is shown in detail in FIGS. 12 and 13 and corresponds substantially to the structure according to FIGS. 3 to 10. In the event of a downward movement of the piston 10 in the direction of the lower chamber delimitation, the air in both flexion chambers 20 is compressed, and at the same time the outlet channel 30 is closed by the closure element 40. In the event of the reverse movement, the closure element 40 remains stuck against the cylinder wall on account of the friction, until the lower side wall of the piston ring groove 14 slides the closure element 40 upwardly. Due to the movement within the piston ring groove 14, the outlet channel 30 is opened and compressed air can escape past the closure element, through the outlet channel 30 and the sound damper 35, into the surrounding environment. An uncontrolled escape is prevented by the upper ring seal 17.

Figure 12:
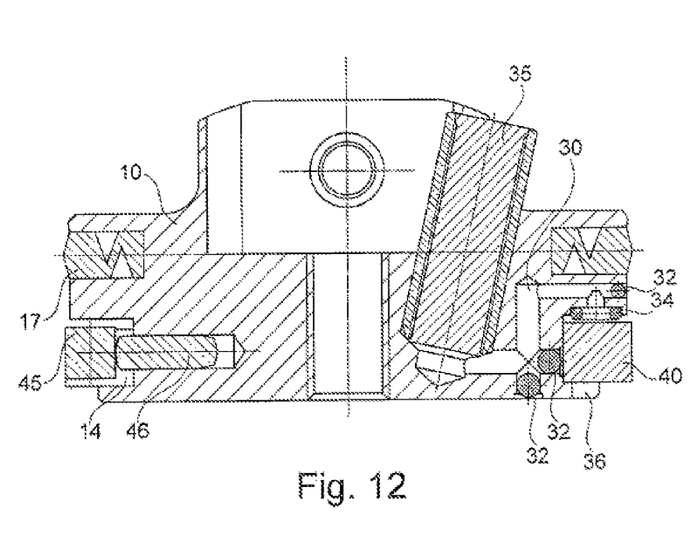
FIG. 12 shows a detailed view of a piston according to FIG. 11 with an open closure element.

The structure of the piston 10 is shown in FIG. 12 in an enlarged sectional illustration. The piston 10 is located in the extension position, i.e. the closure element 40 does not bear against the ring seal 34, such that air from the flexion chamber 20 can flow past the piston ring 40, for example in the region of the bore 36 for the outlet channel 30, in the upper piston ring groove side wall into the outlet channel 30. The air passes from the outlet channel 30 into the surrounding environment via the sound damper 35.

Figure 13:
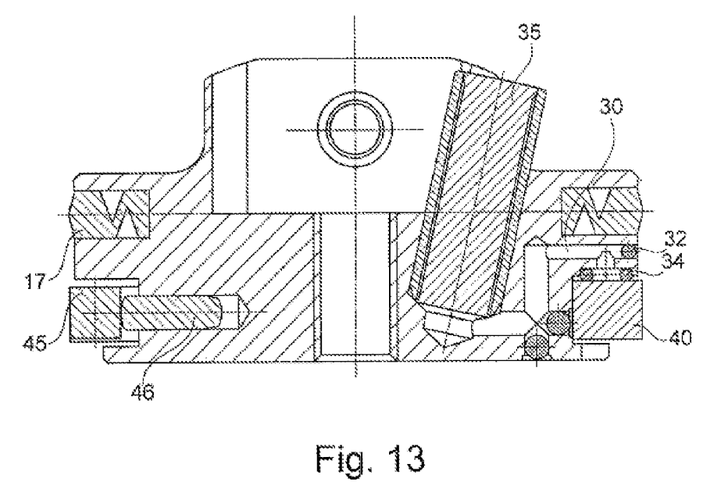
FIG. 13 shows an illustration according to FIG. 12 with a closed closure element.

FIG. 13 shows the detailed illustration according to FIG. 12 in the flexion position, in which the closure element 40 bears sealingly against the ring seal 34, the outlet channel 30 is closed with respect to the flexion chamber 20, and the damping device can compress the air in the flexion chamber as desired.

Figure 14:
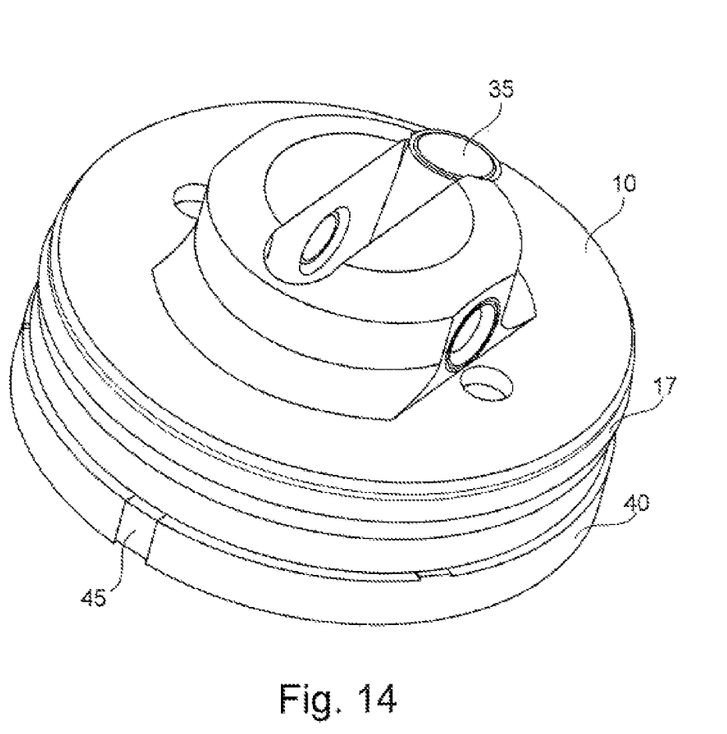
FIG. 14 shows a perspective illustration of a piston according to FIG. 12 or 13.

FIG. 14 shows a perspective enlarged illustration of the piston 10 with the ring seal 17 with the closure element 40 and the widening tensioning element 45.

In the previous exemplary embodiments the upper flexion chamber 20 was always vented. Of course, it is also conceivable to vent the lower flexion chamber 20 additionally or alternatively. In this case the outlet channel 30 is guided as a second bore through the piston rod 80, such that a venting into the atmosphere is made possible in this way. Of course, an extension chamber can also be vented in a similar manner.

In particular, the closure element 40 can also be positioned better and more reliably by means of the tensioning element 45. In accordance with a specific embodiment a tensioning element 45 with oval cross section is to be inserted into an oval recess provided for this purpose in the region of the piston ring slot.

In this way, not only a rotation, but also a torsion of the piston ring is prevented.

Figure 15:
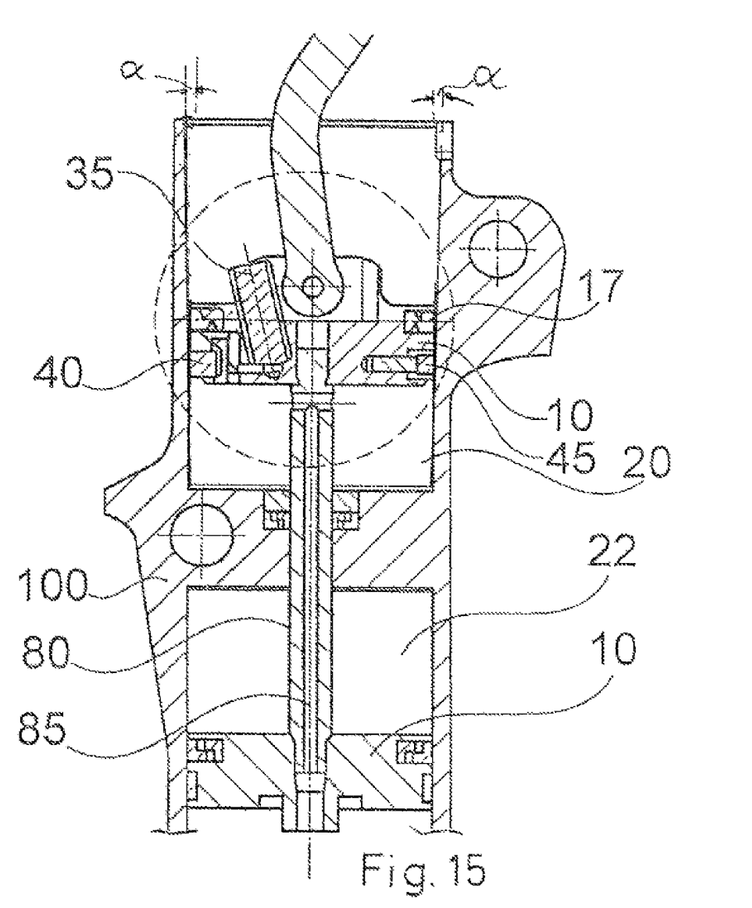
FIG. 15 shows a variant of FIG. 11.

In FIG. 15 a variant of FIG. 11 is illustrated, on the basis of which it is shown in an exemplary manner that the chamber 20 or the cylinder, in which the piston 10 is moved in a longitudinally displaceable manner, has a conical widening upwardly in the illustrated exemplary embodiment, such that, in the event of a flexion movement of a prosthetic knee joint, the gap always provided between the piston 10 and the chamber wall becomes increasingly smaller. In the illustrated exemplary embodiment the cone angle α is approximately 1°, however the conicity may deviate from this in principle. The cone angle α is dimensioned such that both at the upper and the lower reversal point of the piston movement, a displaceability within the chamber 20 is provided and a sufficient sealing via the ring seal is ensured. The closure element 40 slides along the inner side of the chamber 20 and is pressed against the chamber wall by the radially acting tensioning element 45. With increasing flexion and a movement of the piston 10 downwardly, the pressure of the closure element 40 on the inner wall increases on account of the reducing gap between the piston 10 and the chamber inner wall, which leads to an increased friction, and therefore an improved switching capacity of the closure element in the end region of the stroke is provided. As soon as a movement reversal takes place, the closure element 40 sticks better to the chamber wall on account of the higher pressing force, such that the outlet channel 30 opens reliably. Besides the illustrated steady conical tapering in the flexion direction, i.e. in the direction of the lower reversal point, it is also possible to generate different pressing force levels by means of a stepped conical embodiment. It is thus possible, in the upper region, i.e. in the region of the maximum extension, to provide a cylindrical or practically cylindrical embodiment of the chamber 20, whereas an increasing tapering or an enlargement of the cone angle α is provided approximately from the middle of the stroke movement, on the one hand in order to ensure an easy movability in the event of a small flexion, and on the other hand to ensure an improved switching reliability in the event of a high flexion or maximum flexion. In a variant according to FIG. 1 the piston rod 80 is provided with different diameters, wherein the piston rod 80 has a cross section becoming larger upwardly, preferably a conical enlargement, such that the switching element 75, with an increasing flexion of the joint and a movement of the piston 10 downwardly, bears against the piston rod 80 externally with an increasing stress. The conical widening of the piston rod 80 can be formed only in some regions, preferably in the region of the end position of the piston 10, and the widening also does not have to be formed with a constant gradient, and instead the conicity can change over the movement range.

In FIG. 15 it can be seen that the piston rod 80 passes through the blocking element separating the two chambers 20 from one another. The lower chamber 20 is fluidically connected to the upper chamber 20 via a longitudinal bore and a transverse bore in the piston rod 80, such that a venting of the upper chamber 20 into the second chamber 22 or the free surrounding environment simultaneously also causes a venting of the lower chamber 20. The spring-back effect at the end of the flexion phase is prevented due to the venting with pressure relief.

Due to the opening in the outlet channel it is possible in the event of a movement reversal to transfer the overpressure in the first chamber 20 into the surrounding environment or into a second chamber 22, such that the air compressed during the flexion is discharged into the surrounding atmosphere, such that a complete pressure compensation takes place.

The invention claimed is:

1. An orthopedic damping device, comprising:
   a movably mounted piston;
   at least one chamber which has a wall;
   a compressible medium configured to be compressed within the at least one chamber by moving the piston in a first direction and decompressed by moving the piston in an opposite, second direction;
   wherein:
      the at least one chamber is connected to an outlet channel,
      the outlet channel is connected in flow communication with a surrounding atmosphere,
      the outlet channel is assigned a closure element,
      the closure element is slidably mounted on a support, the closure element controlling release of the compressible medium to the surrounding atmosphere,
      the support is at least one of coupled to the piston or formed as the piston, and
      the closure element is coupled to a contact region.

2. The damping device as claimed in claim 1, wherein the contact region is one of the wall of the at least one chamber or a wall of a blocking element.

3. The damping device as claimed in claim 1, wherein the piston is formed as one of a rotary piston or a cylindrical piston.

4. The damping device as claimed in claim 1, wherein the outlet channel leads into the surrounding atmosphere and a second chamber.

5. The damping device as claimed in claim 1, wherein a sound damper is arranged in or on the outlet channel.

6. The damping device as claimed in claim 1, wherein the closure element is mounted frictionally and slidingly on the contact region.

7. The damping device as claimed in claim 1, wherein the closure element is resiliently preloaded against the contact region.

8. The damping device as claimed in claim 1, wherein the outlet channel is guided through the piston.

9. The damping device as claimed in claim 1, wherein the closure element is formed as a piston ring and is mounted in a piston ring groove.

10. The damping device as claimed in claim 1, wherein the closure element is one of mounted on a piston rod and mounted in a blocking element surrounding the piston rod.

11. The damping device as claimed in claim 1, wherein the closure element in a closing state bears against a seal surrounding the outlet channel.

12. The damping device as claimed in claim 4, wherein the second chamber is arranged on a side of the piston opposite the at least one chamber, and the compressible medium is compressed in the second chamber.

13. The damping device as claimed in claim 10, wherein when the closure element is mounted in the blocking element, the blocking element is mounted in a stationary manner in a housing forming the at least one chamber.

14. The damping device as claimed in claim 1, wherein the closure element is coupled to the piston via a switching element.

15. The damping device as claimed in claim 1, wherein at least one of the closure element and the outlet channel is adjustable.

16. The damping device as claimed in claim 1, wherein the chamber tapers conically in a direction of an end position of the piston.

17. The damping device as claimed in claim 1, wherein the support is arranged in a stationary manner inside the at least one chamber.

18. The damping device as claimed in claim 4, wherein the second chamber is formed as an open chamber and has a lower internal pressure than the at least one chamber.

19. An orthopedic damping device, comprising:
a housing;
at least one chamber positioned within the housing;
a piston movably mounted in the at least one chamber, wherein the piston compresses a compressible medium when moving in a first direction and decompresses the compressible medium when moving in a second direction, the second direction being opposite the first direction;
an outlet channel fluidly connected to the at least one chamber and connected in flow communication with a surrounding atmosphere;
a closure element fluidly connected to the outlet channel, the closure element being operable to control release of the compressible medium to the surrounding atmosphere;
a support coupled to the piston, wherein the closure element is slidably mounted on the support;
a contact region coupled to the closure element.

20. The orthopedic damping device of claim 19, further comprising:
a blocking element surrounding the piston rod, wherein the closure element is mounted on the blocking element.

21. The orthopedic damping device of claim 19, wherein the compressible medium is retained in the at least one chamber when the outlet channel is closed, and the compressible medium is released from the at least one chamber when the outlet channel is open.

22. The orthopedic damping device of claim 1, wherein the compressible medium is retained in the at least one chamber when the outlet channel is closed, and the compressible medium is released from the at least one chamber when the outlet channel is open.

23. The orthopedic damping device of claim 1, wherein the closure element is movable relative to the support.

24. An orthopedic damping device, comprising:
a movably mounted piston;
at least one chamber which has a wall;
a compressible medium configured to be compressed within the at least one chamber by moving the piston in a first direction and decompressed by moving the piston in an opposite, second direction;
wherein:
the at least one chamber is connected to an outlet channel,
the outlet channel is assigned a closure element,
the closure element is slidably mounted on a support,
the support is at least one of coupled to the piston or formed as the piston, and
the closure element is coupled to a contact region,
the closure element is formed as a piston ring and is mounted in a piston ring groove.

25. An orthopedic damping device, comprising:
a movably mounted piston;
at least one chamber which has a wall;
a compressible medium configured to be compressed within the at least one chamber by moving the piston in a first direction and decompressed by moving the piston in an opposite, second direction;
wherein:
the at least one chamber is connected to an outlet channel,
the outlet channel is assigned a closure element,
the closure element is slidably mounted on a support,
the support is at least one of coupled to the piston or formed as the piston, and
the closure element is coupled to a contact region,
the contact region is a wall of a blocking element,
the blocking element is mounted in a stationary manner in a housing forming the at least one chamber.

26. An orthopedic damping device, comprising:
a movably mounted piston;
at least one chamber which has a wall and tapers conically in a direction of an end position of the piston;
a compressible medium configured to be compressed within the at least one chamber by moving the piston in a first direction and decompressed by moving the piston in an opposite, second direction;
wherein:
the at least one chamber is connected to an outlet channel,
the outlet channel is assigned a closure element,
the closure element is slidably mounted on a support,
the support is at least one of coupled to the piston or formed as the piston, and
the closure element is coupled to a contact region.

27. An orthopedic damping device, comprising:
a movably mounted piston;
at least one chamber which has a wall;
a compressible medium configured to be compressed within the at least one chamber by moving the piston in a first direction and decompressed by moving the piston in an opposite, second direction;
wherein:
the at least one chamber is connected to an outlet channel,
the outlet channel is assigned a closure element,
the closure element is slidably mounted on a support,
the support is at least one of coupled to the piston or formed as the piston, and the closure element is coupled to a contact region,
the outlet channel leads into at least one of a surrounding atmosphere or a second chamber,
the second chamber is formed as an open chamber and has a lower internal pressure than the at least one chamber.

\* \* \* \* \*